United States Patent
Arsenault et al.

(10) Patent No.: US 10,957,459 B2
(45) Date of Patent: Mar. 23, 2021

(54) SUSPENSION DEVICE FOR A RADIOPROTECTION GARMENT

(71) Applicant: NEWTON MEDICAL INC., Quebec (CA)

(72) Inventors: Jean Arsenault, Quebec (CA); Normand Boiteau, Quebec (CA)

(73) Assignee: NEWTON MEDICAL INC., Quebec (CA)

(*) Notice: Subject to any disclaimer, the term of this patent is extended or adjusted under 35 U.S.C. 154(b) by 0 days.

(21) Appl. No.: 16/487,527

(22) PCT Filed: Mar. 5, 2018

(86) PCT No.: PCT/IB2018/051404
§ 371 (c)(1),
(2) Date: Aug. 21, 2019

(87) PCT Pub. No.: WO2018/163049
PCT Pub. Date: Sep. 13, 2018

(65) Prior Publication Data
US 2020/0058415 A1 Feb. 20, 2020

Related U.S. Application Data

(60) Provisional application No. 62/468,038, filed on Mar. 7, 2017.

(51) Int. Cl.
*G21F 3/02* (2006.01)
*A61B 6/10* (2006.01)

(52) U.S. Cl.
CPC ............... *G21F 3/02* (2013.01); *A61B 6/107* (2013.01)

(58) Field of Classification Search
CPC .................................. G21F 3/02; A61B 6/107
(Continued)

(56) References Cited

U.S. PATENT DOCUMENTS 3,281,598 A 10/1966 Hollstein
3,568,226 A 3/1971 Mater
(Continued)

FOREIGN PATENT DOCUMENTS

CA 2281882 10/2007
CN 102772219 11/2012
(Continued)

OTHER PUBLICATIONS

Written Opinion of the International Searching Authority issued by the World Intellectual Property Organization dated Jun. 19, 2018 for PCT application PCT/IB2018/051404 from which the present application is a national phase entry.
(Continued)

*Primary Examiner* — Michael Maskell

(57) ABSTRACT

A suspension device (10) for at least partially supporting a radioprotection garment (12) worn by an intended user (14), including a harness (34) wearable by the intended user (14) under the radioprotection garment (12), the harness including a harness attachment (38); a support (28) positionable above the intended user (14); an elongated flexible element (30) operatively coupled to the support (28) to be supported thereby; a flexible element attachment (32) secured to the elongated flexible element (30) opposed to the support (28); the harness (34) and flexible element attachment (38) being reversibly attachable to each other.

20 Claims, 5 Drawing Sheets

(58) Field of Classification Search
USPC .................. 250/516.1, 517.1, 519.1
See application file for complete search history.

(56) References Cited

U.S. PATENT DOCUMENTS

| | | |
|---|---|---|
| 3,780,663 A | 12/1973 | Pettit |
| 4,243,147 A | 1/1981 | Twitchell et al. |
| 4,254,341 A | 3/1981 | Herr |
| 4,571,758 A | 2/1986 | Samuelsson |
| 4,673,154 A | 6/1987 | Karapita |
| 5,015,864 A | 5/1991 | Maleki |
| 5,325,550 A | 7/1994 | Dearstyne et al. |
| 5,337,908 A | 8/1994 | Beck, Jr. |
| 5,456,655 A | 10/1995 | Morris |
| 5,623,948 A | 4/1997 | Van Morris |
| 6,035,465 A | 3/2000 | Rogozinski |
| 6,315,138 B1 | 11/2001 | Dyson |
| 6,434,329 B1 | 8/2002 | Dube et al. |
| 6,869,217 B2 | 3/2005 | Rasche et al. |
| 7,291,097 B1 | 11/2007 | Dace et al. |
| 7,462,138 B2 | 12/2008 | Shetty et al. |
| 7,506,589 B2 | 3/2009 | Hjort |
| 7,608,847 B2 | 10/2009 | Rees |
| 7,676,865 B2 | 3/2010 | Graham et al. |
| 7,930,775 B2 | 4/2011 | Kluckhuhn |
| 7,973,299 B2 | 7/2011 | Rees |
| 7,993,248 B1 | 8/2011 | Rasmussen |
| 8,198,616 B2 | 6/2012 | Rees |
| 8,207,516 B2 | 6/2012 | Rees |
| 8,558,204 B2 | 10/2013 | Rees |
| 8,598,554 B2 | 12/2013 | Rees |
| 8,651,343 B2 | 2/2014 | Huang |
| 8,674,330 B2 | 3/2014 | Beck |
| 8,933,426 B2* | 1/2015 | Rees .................. A61B 6/4423 250/516.1 |
| 9,198,470 B1 | 12/2015 | Monir |
| 9,349,492 B1 | 5/2016 | Ganus |
| 9,852,598 B1 | 12/2017 | Thompson |
| 2007/0138415 A1* | 6/2007 | Rees .................. G21F 3/02 250/516.1 |
| 2009/0184269 A1* | 7/2009 | Rees .................. A61B 6/107 250/516.1 |
| 2010/0107320 A1* | 5/2010 | Rees .................. A61B 6/4423 2/456 |
| 2013/0092810 A1* | 4/2013 | Miller ................ A61B 6/107 248/342 |
| 2015/0321031 A1 | 11/2015 | Monn |
| 2017/0087392 A1 | 3/2017 | Lambert et al. |

FOREIGN PATENT DOCUMENTS

| | | |
|---|---|---|
| DE | 2934955 | 3/1981 |
| EP | 94704 | 11/1983 |
| GB | 2457984 | 6/2010 |
| WO | 1996033335 | 10/1996 |

OTHER PUBLICATIONS

International Search Report issued by the World Intellectual Property Organization dated Jun. 19, 2018 for PCT for PCT application PCT/IB2018/051404 from which the present application is a national phase entry.

* cited by examiner

SUSPENSION DEVICE FOR A RADIOPROTECTION GARMENT

The present application claims priority from U.S. provisional patent application 62/468,038 filed Mar. 7, 2017, the contents of which is incorporated by reference in its entirety.

FIELD OF THE INVENTION

The present invention relates to the general field of radioprotection, and is more particularly concerned with a suspension device for a radioprotection garment.

BACKGROUND

Some medical procedures require that the patient be irradiated with X-rays to visualize surgical instrument and anatomical structures during the procedure. Any medical personnel close to the patient while the latter is irradiated must be protected from this radiation. Critically, the main operator must remain close to the patient and as such usually wears a lead apron with a high lead equivalency protection, given his proximity with the source of the x-ray scatter.

Over years and decades, wearing heavy aprons on a daily or weekly basis can lead to orthopaedic strains that can limit or end the career of interventionists. Also, on the shorter term, fatigue may become important for longer interventions. Such fatigue and the associated discomfort can eventually affect the quality of the medical procedure that is performed.

Accordingly, there exists a need for devices and methods to reduce the effect of the weight of radioprotection garments on medical personnel wearing such garments. An object of the invention is to provide such devices and methods.

SUMMARY OF THE INVENTION

In a broad aspect, there is provided a suspension device for at least partially supporting a radioprotection garment while the radioprotection garment is worn by an intended user, the suspension device comprising: a harness wearable by the intended user under the radioprotection garment, the harness including a harness attachment; a support positionable above the intended user; an elongated flexible element operatively coupled to the support to be supported thereby; a flexible element attachment secured to the elongated flexible element opposed to the support; the harness and flexible element attachment being reversibly attachable to each other. When the harness and flexible element attachments are attached to each other and a tension is applied to the elongated flexible element, at least part of a weight of the radioprotection garment is supported by the support through the elongated flexible element.

There may also be provided a suspension device wherein the harness includes a substantially rigid harness support portion, the harness attachment being secured to the harness support portion.

There may also be provided a suspension device wherein the flexible element attachment includes an attachment portion attachable to the harness attachment and a linking portion extending from the attachment portion, the linking portion defining a flexible element receiving portion, the elongated flexible element being secured to the flexible element receiving portion.

There may also be provided a suspension device wherein the harness attachment includes an anterior abutment portion and a posterior abutment portion defining a gap therebetween, the anterior abutment portion being closer to the harness support portion than the posterior abutment portion, the posterior abutment portion being higher than the anterior abutment portion when the suspension device is operatively used to support the radioprotection garment; the attachment portion defines an anterior abutment surface and a posterior abutment surface; the attachment portion is insertable in the gap between the anterior and posterior abutment portions and movable relative thereto between an engaged position and a disengaged position, wherein, in the engaged position, the anterior and posterior abutment surfaces abut respectively against the anterior and posterior abutment portions, and in the disengaged position, at least one of the anterior and posterior abutment surfaces is spaced apart from respectively the anterior and posterior abutment portions to allow removal of the attachment portion from the gap, the anterior and posterior abutment surfaces and the anterior and posterior abutment portions being configured and sized so that translation between the attachment portion and the harness attachment is prevented with the attachment portion in the engaged position.

There may also be provided a suspension device wherein in the disengaged position, the attachment portion is pivoted relative to a position of the attachment portion in the engaged position.

There may also be provided a suspension device wherein the harness attachment includes a frame, an anterior abutment member mounted to the frame and a posterior abutment member mounted to the frame, the anterior and posterior abutment members defining respectively the anterior and posterior abutment portions.

There may also be provided a suspension device wherein the anterior and posterior abutment members are substantially elongated and substantially parallel to each other.

There may also be provided a suspension device wherein the attachment portion is substantially plate-shaped and defines a concave groove defining the anterior abutment surface and receiving the anterior abutment member thereinto in the engaged position.

There may also be provided a suspension device wherein at least one of the anterior and posterior abutment surfaces is concave.

There may also be provided a suspension device wherein the harness attachment includes an anterior abutment portion and a posterior abutment portion defining a gap therebetween and a gap access leading into the gap, the anterior abutment portion being closer to the harness support portion than the posterior abutment portion, the posterior abutment portion being closer to the gap access than the anterior abutment portion; the attachment portion defines an anterior abutment surface and a posterior abutment surface; the attachment portion is insertable in the gap between the anterior and posterior abutment portions through the gap access and movable relative thereto between an engaged position and a disengaged position, wherein, in the engaged position, the anterior and posterior abutment surfaces abut respectively against the anterior and posterior abutment portions, and in the disengaged position, at least one of the anterior and posterior abutment surfaces is spaced apart from respectively the anterior and posterior abutment portions and removable from the gap, the anterior and posterior abutment surfaces and the anterior and posterior abutment portions being configured and sized so that translation between the attachment portion and the harness attachment is prevented with the attachment portion in the engaged position.

There may also be provided a suspension device wherein the flexible element receiving portion and the attachment portion are substantially vertically aligned relative to each other when the suspension device is operatively used to support the radioprotection garment.

There may also be provided a suspension device wherein the flexible element receiving portion and the attachment portion are substantially vertically aligned relative to each other when the flexible element attachment freely hangs from the elongated flexible element.

There may also be provided a suspension device wherein the linking portion is substantially arcuate.

There may also be provided a suspension device wherein the harness support portion includes a back portion and a pair of shoulder portions extending each from the back portion, the back and shoulder portions being configured and sized for extending respectively substantially parallel to a back and over the shoulders of the intended user when the harness is operatively worn by the intended user.

There may also be provided a suspension device wherein the harness attachment is secured to the back portion.

There may also be provided a suspension device wherein the support is mountable to a ceiling.

There may also be provided a suspension device wherein the support includes a base mountable to the ceiling and an arm mounted to the base, the elongated flexible element being mounted to the arm.

There may also be provided a suspension device wherein the arm is pivotable relative to the base about a substantially vertical axis when the support is operatively mounted to the ceiling.

There may also be provided a suspension device wherein the arm is telescopic so that a distance between the elongated flexible element and the base is varied as the arm is extended and retracted.

There may also be provided a suspension device further comprising a balancer between the elongated flexible element and the support.

There may also be provided a suspension device wherein the elongated flexible element is a cable.

In another broad aspect, there is provided a suspended radioprotection garment, comprising the suspension device as recited above in this document; and a radioprotection garment at least partially supported by the suspension device.

There may also be provided a suspended radioprotection garment wherein the radioprotection garment is worn over the harness.

Advantageously, the proposed suspension device supports at least part of the weight of the radioprotection garment, and in some embodiments almost or totally the whole weight of the radioprotection garment. This reduces, fatigue, discomfort and the potential for repetitive stress injuries for the intended user.

Other objects, advantages and features of the present invention will become more apparent upon reading of the following non-restrictive description of preferred embodiments thereof, given by way of example only with reference to the accompanying drawings.

DETAILED DESCRIPTION

The term "substantially" is used throughout this document to indicate variations in the thus qualifies terms. These variations are variations that do not materially affect the manner in which the invention works and can be due, for example, to uncertainty in manufacturing processes or to small deviations from a nominal value that do not cause significant changes to the invention. These variations are to be interpreted from the point of view of the person skilled in the art. Also, directional terminology such as anterior and upper, among others, is used in this document and refer to the proposed suspension device 10 in a typical operational configuration supporting a radioprotection garment 12 worn by an intended user 14 from above. This terminology is used for clarity reasons and should not be used to restrict the scope of the appended claims unless explicitly mentioned in the claims.

Figure 1:
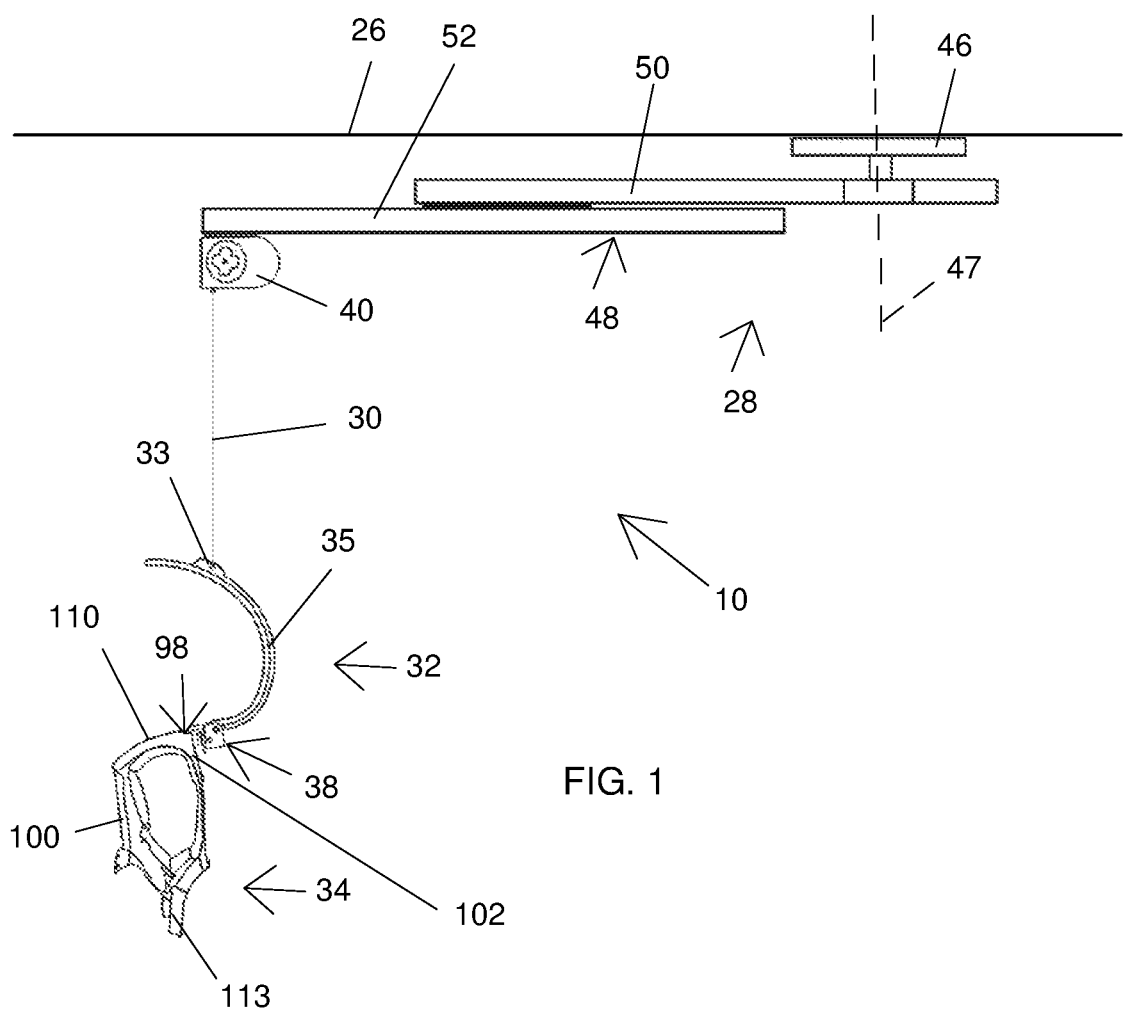
FIG. 1, in a side elevation view, illustrates a suspension device in accordance with an embodiment of the present invention.
Figure 2:
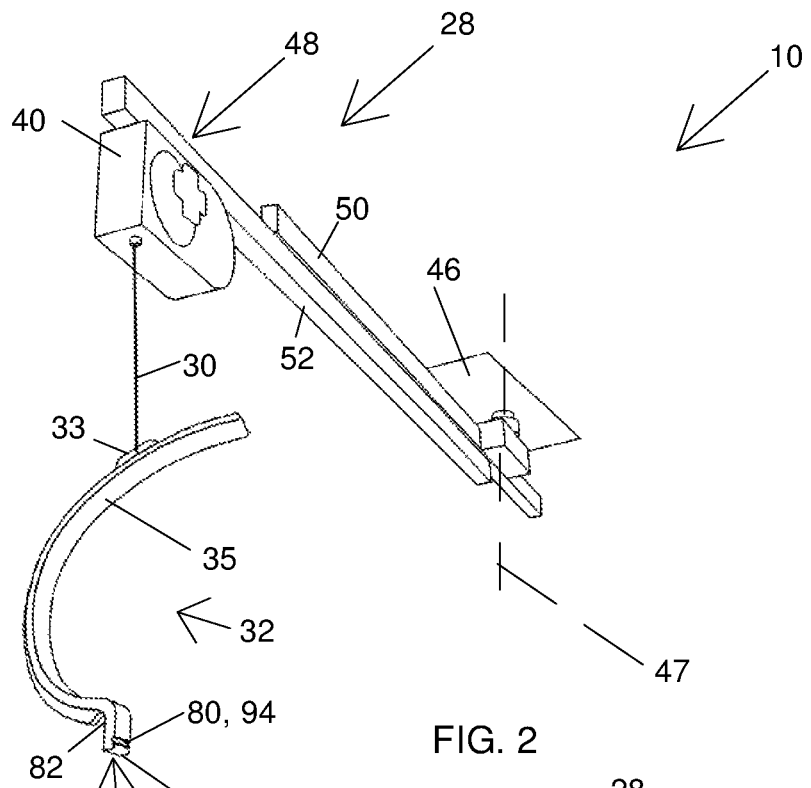
FIG. 2, in a partial perspective view, illustrates the suspension device of FIG. 1 in a first configuration.
Figure 4:
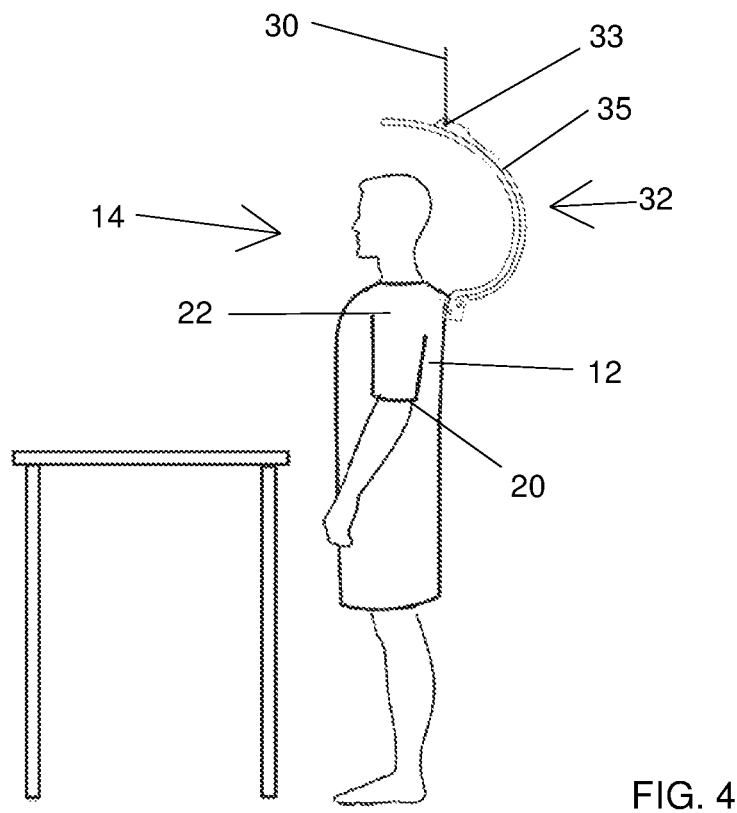
FIG. 4, in a partial side elevation view with parts removed, illustrates an intended user wearing a radioprotection garment supported by the suspension device of FIGS. 1 to 3.

Referring to FIG. 1, there is shown the suspension device 10 for at least partially supporting the radioprotection garment 12, as shown in FIG. 4. Still referring to FIG. 4, the radioprotection garment 12 may be worn by an intended user 14 to protect against radiation. The radioprotection garment 12 may be for example a lead apron, as seen in FIG. 2, or a combination lead vest and lead skirt (not shown in the drawings). It should be noted that the terminology "lead apron" is commonly used in the art, but that it refers to radioprotection garments that may or may not include lead.

The radioprotection garment 12 defines a pair of armholes 20, only one of which is shown in FIG. 4. Each armhole 20 is delimited at the top by a shoulder area 22. Each shoulder area 22 is positioned over one of the shoulders 27 of the intended user 14 (seen in FIG. 5) when the radioprotection garment 12 is worn.

Referring to FIG. 1, the suspension device 10 includes a support 28 positionable above the intended user 14 (not shown in FIG. 1), an elongated flexible element, for example a cable 30, a flexible element attachment, for example a cable attachment 32, and a harness 34. The support 28 may be temporarily or permanently fixed to the ceiling 26 of a room where the intended user 14 will use the suspension device 10. The cable 30 is operatively coupled to the support 28 so as to be supported thereby, either by being directly mounted thereto or indirectly mounted thereto with other components therebetween. The cable attachment 32 is secured the cable 30 opposed to the support 28. The harness 34 is wearable by the intended user 14 under the radioprotection garment 12 between the shoulders 27 of the intended user 14 and the shoulder area 22 of the radioprotection garment 12 (not shown in FIG. 1). The harness 34 includes a harness attachment 38. The harness and cable attachments 38 and 32 are reversibly attachable to each other.

When the harness and cable attachments 38 and 32 are attached to each other and a tension is applied to the cable 30, at least part of a weight of the radioprotection garment 12 can be supported by the support 28 through the cable 30. Thus, when the harness 34 is worn under the radioprotection garment 12 and suspended by the cable 30, at least some of the weight of the radioprotection garment 12 may be supported by the cable 30, therefore reducing the apparent weight of the radioprotection garment 12. In some embodiments, a balancer 40 is provided between the cable 30 and the support 28 for exerting a predetermined tension on the cable 30. With a suitable tension, the apparent weight of the radioprotection garment 12 can be close to any desired value between zero and the unsuspended weight thereof, for example close to zero. The balancer 40 may be adjustable so that the tension can be adjusted. The cable 30 can also be wound in the balancer or unwound therefrom.

If the radioprotection garment 12 is a one-piece radioprotection garment 12, suspending the harness 34 supports the whole radioprotection garment 12. If the radioprotection garment 12 includes the lead vest and lead skirt only the lead vest is directly suspended by the cable 30. In such cases, the lead skirt may be supported by the intended user 14 in a conventional manner, or skirt supports (not shown in the drawings) may be used to suspend the lead skirt from the lead vest, such that when the lead vest is supported by the suspension device 10, at least part of the weight of the lead skirt is also supported by the suspension device 10.

Figure 3:
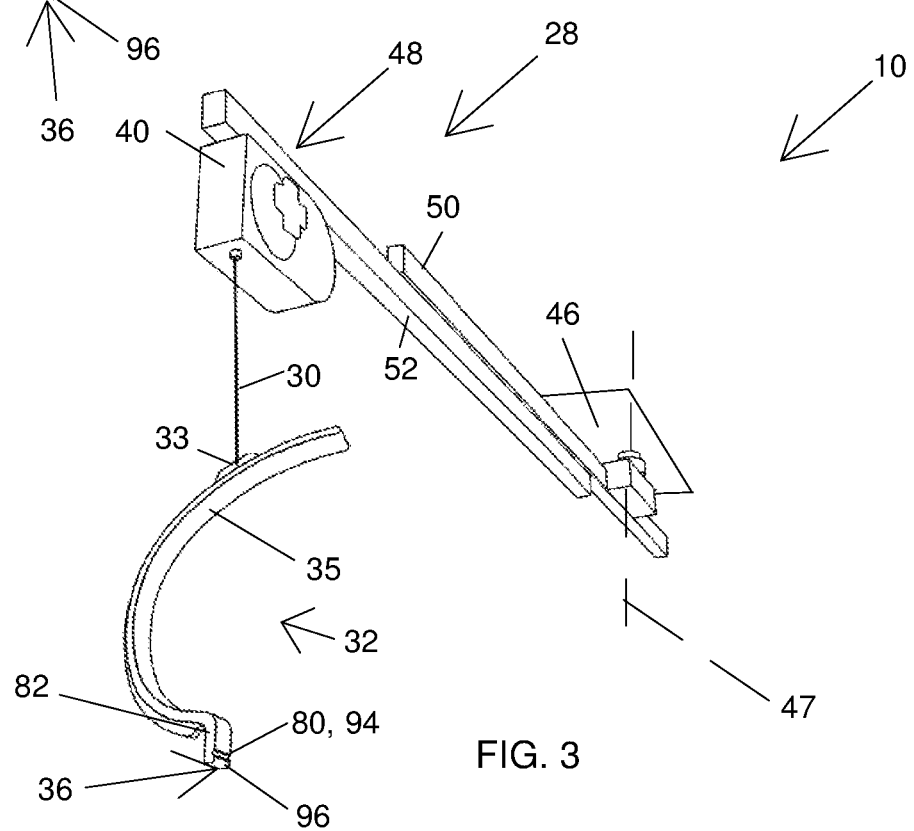
FIG. 3, in a partial perspective view, illustrates the suspension device of FIGS. 1 and 2 in a second configuration.

Referring to FIGS. 1, 2 and 3, the support 28 is any element that may be used to suspend the cable 30 from a ceiling 26 (only shown in FIG. 1). In some embodiments, not shown in the drawings, the support 28 is simply a hook or other similar hardware secured to the ceiling 26. In other embodiments, as seen in FIG. 1, the support 28 is configured to allow the intended user 14 to move in the room in which the suspension device 10 is provided. For example, the support 28 includes a base 46, which can be fixedly secured to the ceiling 26, and an arm 48 pivotably mounted to the base 46 so at to pivot about a substantially vertical axis 47.

In some embodiments, not shown in the drawings, the cable 30 is fixedly secured to a fixed length arm. In other embodiments, also not shown in the drawings, the cable 30 is mounted to the arm so as to be movable therealong, for example using rollers. In yet other embodiments, as shown in FIGS. 1 to 3, the cable 30 is mounted to a telescopic arm 48 including arm first and second elements 50 and 52, each substantially elongated and longitudinally movable relative to each other. The arm 48 is for example substantially horizontal, but angled arms are also within the scope of the invention. The arm first element 50 is pivotally mounted to the base 46, and the arm second element 52 is mounted to and movable relative to the arm first element 50. The cable 30 is mechanically coupled to the arm second element 52, for example adjacent one longitudinal end thereof. A distance between the cable 30 and the base 46 is varied as the arm 48 is extended and retracted Thus, by combination of elongation and retraction of the telescopic arm 48 and pivotal movements of the telescopic arm 48 about the base 46, the intended user 14 can move over a predetermined area to access different anatomical features of a patient or to fetch or dispose of surgical instruments, for example.

The pivotable attachment of the arm 48 to the base 46 and the telescopic structure of the arm 48 may be achieved in any suitable manner known in the art. The specific structure used to that effect is therefore not described in further details herein. Also, while a specific example of a support 28 has been described and many other examples of suitable support have been mentioned, any other suitable support able to support the cable 30 above the intended user 14 are usable with the invention.

When present, the balancer 40 is secured to the arm second element 52. For example, the balancer 40 is a constant tension tool retractor. The balancer 40 provides a constant tension independent of the length of the cable 30 that is mounted thereto, which can be wound on a reel (not shown in the drawings) located in the balancer 40 or unwound therefrom. In some embodiments, the balancer 40 may be adapted to a wide range of radioprotection garment 12 weight and to intended users 14 having different heights.

Referring to FIG. 1, the harness 34 includes a substantially rigid harness support portion 98, the harness attachment 38 being secured to the harness support portion 98. In some embodiments, straps (described in further details below) extend from the harness support portion 98. The harness 34 is configured to be worn between the intended user 14 and the radioprotection garment 12. When the suspension device 10 supports the harness 34, the radioprotection garment 12 rests on the harness 34 so that at least part of the weight of the radioprotection garment 12 is supported by the harness 34.

Figure 5:
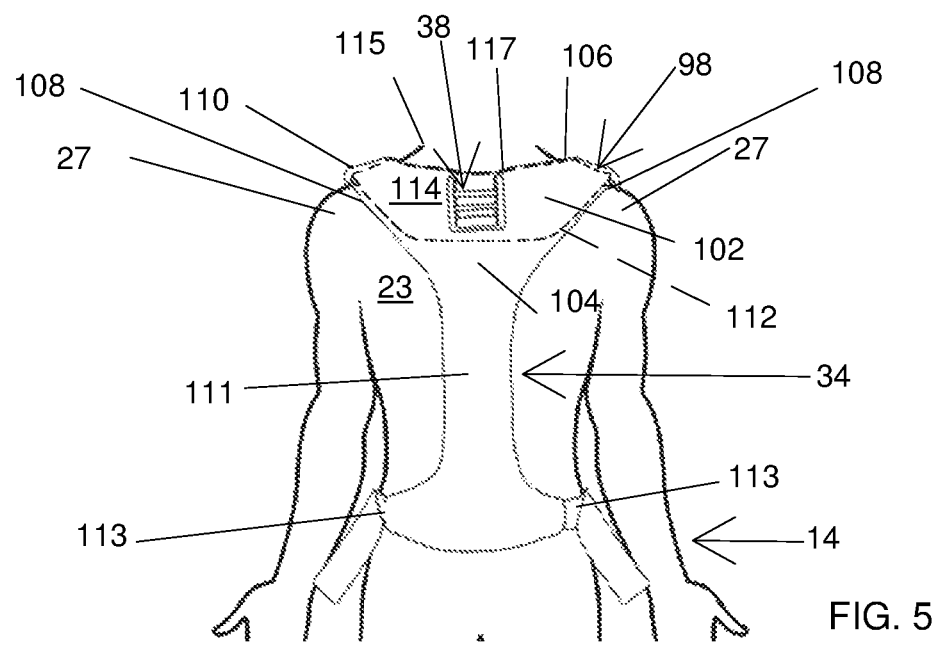
FIG. 5, in a rear elevation view, illustrates the intended user wearing a harness part of the suspension device of FIGS. 1 to 3.

With reference to FIG. 5, in a specific embodiment of the invention, the harness support portion 98 includes a back portion 102 defining opposed back portion bottom and top edges 104 and 106 and a pair of laterally opposed back portion side edges 108 extending therebetween. A pair of laterally opposed shoulder portions 110 extend from the back portion 102 at the back portion top edge 106, each substantially adjacent a respective one of the back portion side edges 108. The shoulder portions 110 extend generally towards the front of the intended user 14 when the harness 34 is worn by the latter. The shoulder portions 110 and the back portion 102 are for example angled between about 75 to about 95 degrees relative to each other. In other embodiments, the shoulder portions 110 and the back portion 102 are angled between about 80 to about 90 degrees relative to each other. The gap between the shoulder portions 110, along with the free portion of the back portion top edge 106 form a neck receiving recess 117 receiving the neck 115 of the intended user 14 in use.

The back and shoulder portions 102 and 110 are configured and sized for extending respectively substantially parallel to a back 23 and over the shoulders 27 of the intended user 14 when the harness 34 is operatively worn by the latter. In some embodiments, better fit to the intended user 14 is provided by manufacturing a custom-fit harness support portion 98 for each intended user.

In some embodiments, the harness support portion 98 has a layered structure. At its core, the harness support portion 98 is made of a substantially rigid core 112, made of substantially rigid material, for example carbon fiber. The core 112 is covered by a coating 114, to protect the core 112 from abrasion and other damages that the radioprotection garment 12 may cause. The coating 114 is for example made of a relatively low-friction material, such as Lycra™. The side of the harness 34 facing the intended user may be covered in part or totally with a resiliently deformable layer (not shown in the drawings), for example including a foam or a gel, to improve comfort.

As seen in FIG. 5, a back strap 111 extends downwardly from the harness support portion 98 at the back portion bottom edge 104. The back strap 11 is terminated opposed to the harness support portion 98 by a pair of laterally opposed hip straps 113. A shoulder strap 100 (better seen in FIG. 1) extends between each one of the shoulder portions 110, for example generally at the front end thereof, and a respective hip strap 113. The shoulder and hip straps 100 and 113 may be a conventional adjustable length strap and are used to secure the harness 34 to the intended user 14. In some embodiments, the hip straps 113 are also attachable to each other at the front of the intended user 14.

The harness attachment 38 is any structure that can be releasably secured to the cable attachment 32. The harness attachment 38 is for example secured to the back portion 102, substantially adjacent the back portion top edge 106, outside the harness 34. The harness attachment 38 is better seen in FIGS. 6 and 7. Advantageously, this position of the harness attachment 38, behind the intended user, greatly reduces sterilization constraints on the suspension device 10. Indeed, international standards do not require that anything behind a person be sterilized when surgery is performed if that person is sterile. Thus, anyone can assist the intended user in attaching the cable attachment 32 to the harness attachment 38 and detaching the cable attachment 32 from the harness attachment 38, even if they are not themselves sterile.

Figure 7:
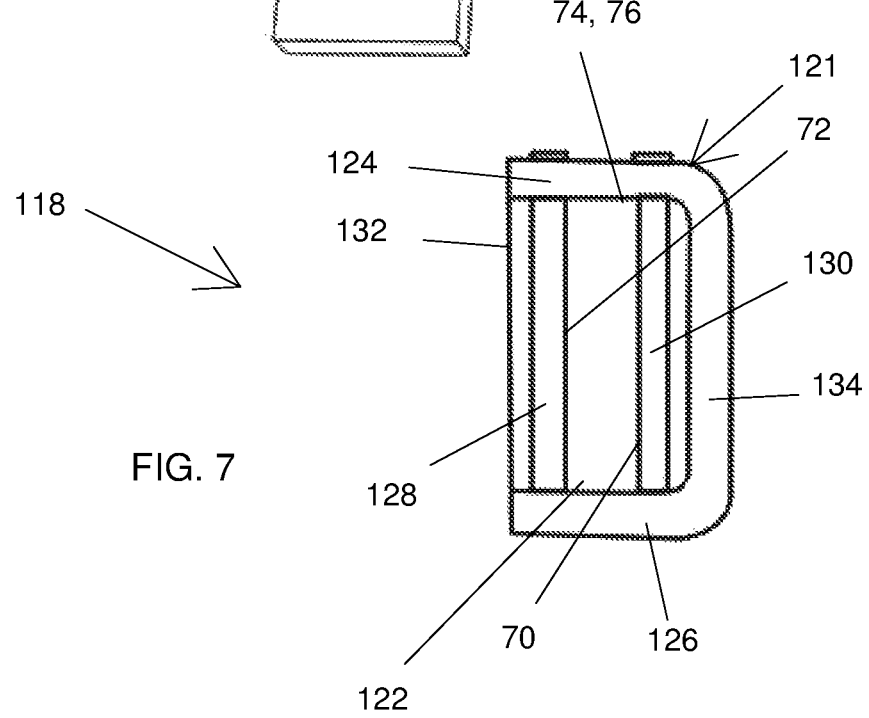
FIG. 7, in a partial top plan view, illustrates the harness attachment of FIG. 6.

Referring for example to FIG. 7, the harness attachment 38 includes an anterior abutment portion 70 and a posterior abutment portion 72 defining a gap 74 therebetween and a gap access 76 leading thereinto. The anterior abutment portion 70 is closer to the harness support portion 98 (not shown in FIG. 7) than the posterior abutment portion 72. The posterior abutment portion 72 is also higher than the anterior abutment portion 70. In other words, the posterior abutment portion 72 is closer to the gap access 76 than the anterior abutment portion 70. The gap access 76 therefore faces generally upwardly when the suspension device 10 is operatively used to support the radioprotection garment 12. As further detailed hereinbelow, the attachment portion 36 is insertable in the gap 74 between the anterior and posterior abutment portions 70 and 72 through the gap access 76 to attach the attachment portion 36 to the harness attachment 38.

Figure 6:
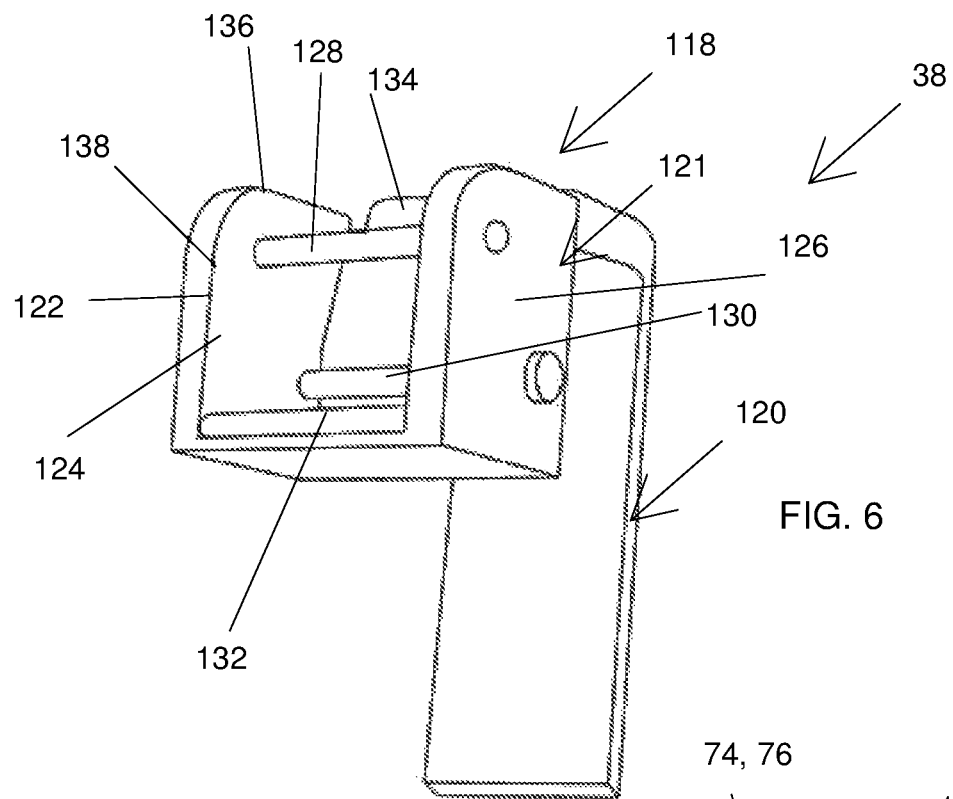
FIG. 6, in a perspective view, illustrates a harness attachment part of the harness of FIG. 5.

Referring to FIG. 6, the harness attachment 38 includes an attachment body 118 mounted to an attachment bracket 120. The attachment bracket 120 is configured for mounting the harness attachment 38 to the back portion 102. For example, the attachment bracket 120 is substantially J-shaped and positioned upside down so as to hang from the back portion 102 at the back portion top edge 106. The attachment bracket 120 may be secured to the back portion 102 in any suitable manner, for example by using an adhesive, a fastener, or by being integrated in the core 112 while the latter is manufactures, among other possibilities.

In a specific embodiment, the attachment body 118 defines a recess 122 for receiving the attachment portion 36 thereinto. For example the recess 122 is defined in a frame 121 including a pair of laterally spaced apart frame side walls 124 and 126. Frame lower and anterior walls 132 and 134 extend each between the frame side walls 124 and 126 and from each other to form a substantially L-shaped structure. The attachment body 118 is in some embodiments mounted to the attachment bracket 120 at the frame anterior wall 134.

An anterior abutment member 130 is mounted to the frame 121, for example in the recess 122. Also, a posterior abutment member 128 is mounted to the frame 121, for example in the recess 122. The anterior and posterior abutment members 130 and 128 define respectively the anterior and posterior abutment portions 70 and 72. For example, the anterior and posterior abutment members 130 and 128 are substantially elongated and substantially parallel to each other. In a specific example of implementation, the posterior and anterior abutment members 128 and 130 take the form of pins extending transversally across the recess 122. The anterior and posterior abutment members 130 and 128 are offset relative to each other so that the posterior abutment member 128 is both further away from the frame lower and anterior walls 132 and 134 than the anterior abutment member 130. However, in alternative embodiments of the invention, the anterior and posterior abutment portions 70 and 72 may be formed in any other suitable manner, for example machined or otherwise formed integrally in a solid piece of material, among other possibilities.

In some embodiments, the posterior abutment member 128 delimits upper and posterior apertures 136 and 138 in the attachment body 118. More specifically, the upper aperture 136 is delimited between the posterior abutment member 128, frame anterior wall 134, and the frame side walls 124 and 126. The posterior aperture 138 is delimited between the posterior abutment member 128, frame lower wall 132, and the frame side walls 124 and 126.

Referring for example to FIG. 3, the cable attachment 32 includes an attachment portion 36 attachable to the harness attachment 38 and a linking portion 35 extending from the attachment portion 36. The linking portion 35 defines a cable receiving portion 33, the cable 30 being secured to the cable receiving portion 33. In some embodiments, the cable 30 may be terminated by an attachment attaching the cable attachment 32 thereto. For example, the attachment is a carabiner mountable to an aperture provided in the cable receiving portion. In other embodiments, the cable 30 is attached through a knot in an aperture provided in the cable receiving portion 33. It should be noted that the cable 30 and the cable attachment 32 may be replaced in alternative embodiment by any suitable elongated flexible element and an attachment configured to be secured thereto, such as a rope, a chain, or a strap, among other possibilities.

The cable attachment 32 is any structure that may attach to the harness 34. For example, the cable attachment 32 includes a substantially arcuate linking portion 35 defining an aperture in the cable receiving portion 33. The arcuate shape of the linking portion 35 allows to clear the head of the intended user 14 when the suspension device 10 is in use. The linking portion 35 is terminated at its lower end by the attachment portion 36. In some embodiments, the cable receiving portion 33 and the attachment portion 36 are substantially vertically aligned relative to each other when the suspension device 10 is operatively used to support the radioprotection garment 12. In some embodiments, the cable receiving portion 33 and the attachment portion 36 are also substantially vertically aligned relative to each other when cable attachment 32 freely hangs from the cable 30. This configuration may in some embodiment facilitate positioning of the cable attachment 32 for attachment to the harness 34. This is achieved by carefully shaping the cable attachment 32 to suitably position its center of mass.

The attachment portion 36 defines an anterior abutment surface 80 and a posterior abutment surface 82, both part of the general outer surface of the attachment portion 36. For example, the attachment portion 36 takes the form of a generally elongated and plate-shaped element provided with a substantially horizontal concave groove 94 extending thereinto substantially adjacent its coupling portion free end 96 and facing towards the anterior abutment member 128 when the attachment portion 36 is attached to the harness attachment 38. The concave groove 94 defines the anterior abutment surface 80.

Figure 9:
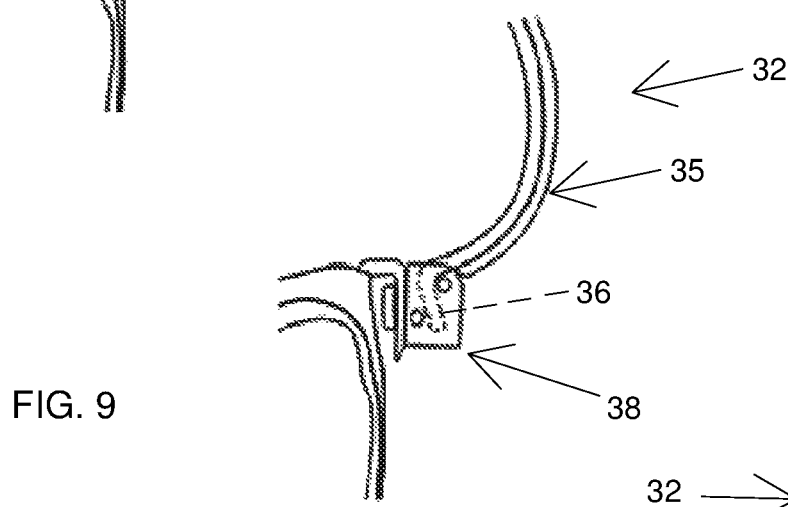
FIG. 9, in a side elevation view, illustrates a second step in the attachment of a cable attachment to the harness attachment.
Figure 10:
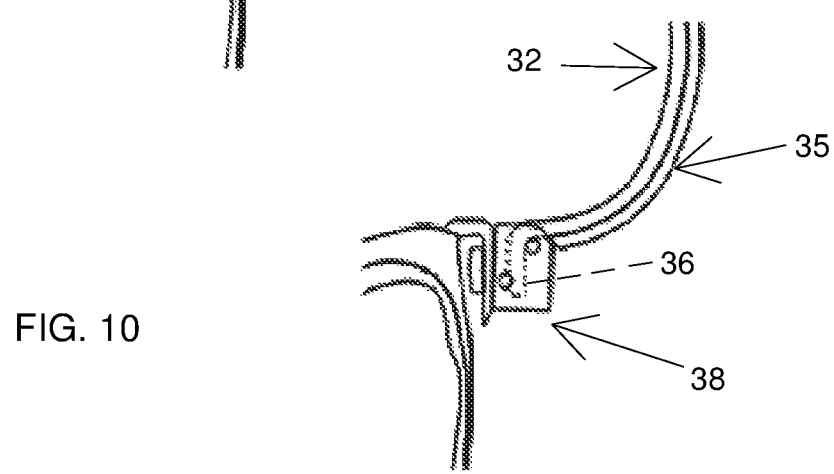
FIG. 10, in a side elevation view, illustrates a third step in the attachment of a cable attachment to the harness attachment.

The attachment portion 36 is insertable in the gap 74 between the anterior and posterior abutment portions 70 and 72 and movable relative thereto between an engaged position (seen in FIG. 9) and a disengaged position (seen in FIG. 10). In the engaged position, the anterior and posterior abutment surfaces 80 and 82 abut respectively against the anterior and posterior abutment portions 70 and 72. In the disengaged position, at least one of the anterior and posterior abutment surfaces 80 and 82 is spaced apart from respectively the anterior and posterior abutment portions 70 and 72 to allow removal of the attachment portion 36 from the gap 74. The anterior and posterior abutment surfaces 80 and 82 and the anterior and posterior abutment portions 70 and 72 are configured and sized so that translation between the attachment portion 36 and the harness attachment 38 is prevented with the attachment portion 36 in the engaged position. Typically, in the disengaged position, the attachment portion 36 is pivoted relative to the position of the attachment portion 36 in the engaged position.

More specifically, the configuration of the recess 122 and posterior and anterior abutment members 128 and 130 is such that when the attachment portion 36 is received in the recess 122 in the engaged position, the attachment portion 36 extends through the upper aperture 136, the anterior abutment member 130 is received at least partially in the groove 94, and the attachment portion 36 abuts against the posterior abutment member 128. In this configuration, the attachment portion 36 cannot be removed from the recess 122 by pulling because of the mechanical interlocking with the anterior abutment member 130. This position is maintained by the combined weight of the harness 34 and radioprotection garment 12 which exert a torque on the harness attachment 34 forcing the attachment portion 36 towards the engaged position.

Figure 8:
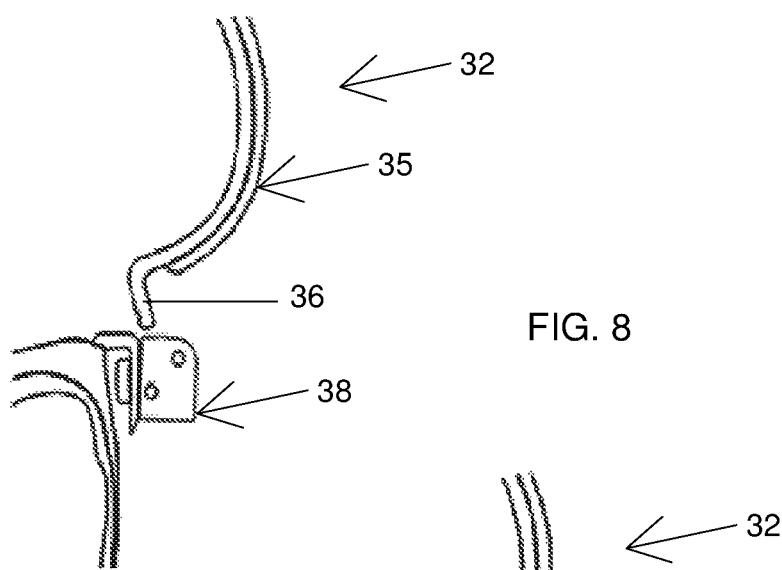
FIG. 8, in a side elevation view, illustrates a first step in the attachment of a cable attachment part of the suspension device of FIGS. 1 to 3 to the harness attachment of FIGS. 5 to 6.

To remove the attachment portion 36 from the harness attachment 38, the former is pivoted about the posterior abutment member 128 so that the anterior abutment member 130 no longer engages the groove 94. In this configuration, the groove 94 is then positioned rearwardly relative to the anterior abutment member 130, as seen in FIG. 8. Then, one can pull on the attachment portion 36 to remove the attachment portion 36 from the recess 122.

Depending on the dimensions of the attachment body 118, the attachment portion 36 may then protrude through the posterior aperture 138. If the attachment body 118 extends backwardly enough, the attachment portion 36 will not protrude through the posterior aperture 138, and the latter could be covered by a wall or left open. This pivotal movement of the attachment portion 36 does not occur spontaneously in use as the combined weight of the harness 34 and radioprotection garment 12 exert a torque in the direction opposed to the direction required to remove the attachment portion 36 from the recess 122.

In use, the intended user 14 first puts on the harness 34, similarly to the manner in which a backpack would be worn, and adjusts the shoulder straps 100 and hip straps 111 to a comfortable length. The intended user 14 then puts on the radioprotection garment 12 in a conventional manner.

Subsequently, the intended user approaches the support 28 and the cable attachment 32 is pulled so that the attachment portion 36 can be inserted at an angle through the top aperture 136, and then pivoted until the anterior abutment member 130 is at least partially received in the groove 94, at which point the cable attachment 32 is released and pulled upwardly by the balancer 40, which consequently reduces or eliminates the apparent weight of the combined harness 34 and radioprotection garment 12. When the radioprotection garment 12 is no longer needed, these operations are reversed.

Although the present invention has been described hereinabove by way of preferred embodiments thereof, it can be modified, without departing from the spirit and nature of the subject invention as defined in the appended claims.

What is claimed is:

1. A suspension device for at least partially supporting a radioprotection garment while the radioprotection garment is worn by an intended user, the suspension device comprising:
   a harness wearable by the intended user under the radioprotection garment, the harness including a harness attachment;
   a support positionable above the intended user;
   an elongated flexible element operatively coupled to the support to be supported thereby;
   a flexible element attachment secured to the elongated flexible element opposed to the support;
   the harness and flexible element attachment being reversibly attachable to each other;
   wherein, when the harness and flexible element attachments are attached to each other and a tension is applied to the elongated flexible element, at least part of a weight of the radioprotection garment is supported by the support through the elongated flexible element;
   further wherein
      the harness includes a substantially rigid harness support portion, the harness attachment being secured to the harness support portion;
      the flexible element attachment includes an attachment portion attachable to the harness attachment and a linking portion extending from the attachment portion, the linking portion defining a flexible element receiving portion, the elongated flexible element being secured to the flexible element receiving portion;
      the harness attachment includes an anterior abutment portion and a posterior abutment portion defining a gap therebetween, the anterior abutment portion being closer to the harness support portion than the posterior abutment portion, the posterior abutment portion being higher than the anterior abutment portion when the suspension device is operatively used to support the radioprotection garment;
      the attachment portion defines an anterior abutment surface and a posterior abutment surface;
      the attachment portion is insertable in the gap between the anterior and posterior abutment portions and movable relative thereto between an engaged position and a disengaged position, wherein, in the engaged position, the anterior and posterior abutment surfaces abut respectively against the anterior and posterior abutment portions, and in the disengaged position, at least one of the anterior and posterior abutment surfaces is spaced apart from respectively the anterior and posterior abutment portions to allow removal of the attachment portion from the gap, the anterior and posterior abutment surfaces and the anterior and posterior abutment portions being configured and sized so that translation between the attachment portion and the harness attachment is prevented with the attachment portion in the engaged position; and in the disengaged position, the attachment portion is pivoted relative to a position of the attachment portion in the engaged position.

2. The suspension device as defined in claim 1, wherein the harness attachment includes a frame, an anterior abutment member mounted to the frame and a posterior abutment member mounted to the frame, the anterior and posterior abutment members defining respectively the anterior and posterior abutment portions.

3. The suspension device as defined in claim 2, wherein the anterior and posterior abutment members are substantially elongated and substantially parallel to each other.

4. The suspension device as defined in claim 3, wherein the attachment portion is substantially plate-shaped and defines a concave groove defining the anterior abutment surface and receiving the anterior abutment member thereinto in the engaged position.

5. The suspension device as defined in claim 1, wherein at least one of the anterior and posterior abutment surfaces is concave.

6. The suspension device as defined in claim 1, wherein
the harness attachment includes an anterior abutment portion and a posterior abutment portion defining a gap therebetween and a gap access leading into the gap, the anterior abutment portion being closer to the harness support portion than the posterior abutment portion, the posterior abutment portion being closer to the gap access than the anterior abutment portion;
the attachment portion defines an anterior abutment surface and a posterior abutment surface;
the attachment portion is insertable in the gap between the anterior and posterior abutment portions through the gap access and movable relative thereto between an engaged position and a disengaged position, wherein, in the engaged position, the anterior and posterior abutment surfaces abut respectively against the anterior and posterior abutment portions, and in the disengaged position, at least one of the anterior and posterior abutment surfaces is spaced apart from respectively the anterior and posterior abutment portions and removable from the gap, the anterior and posterior abutment surfaces and the anterior and posterior abutment portions being configured and sized so that translation between the attachment portion and the harness attachment is prevented with the attachment portion in the engaged position.

7. The suspension device as defined in claim 1, wherein the flexible element receiving portion and the attachment portion are substantially vertically aligned relative to each other when the suspension device is operatively used to support the radioprotection garment.

8. The suspension device as defined in claim 1, wherein the flexible element receiving portion and the attachment portion are substantially vertically aligned relative to each other when the flexible element attachment freely hangs from the elongated flexible element.

9. The suspension device as defined in claim 1, wherein the linking portion is substantially arcuate.

10. The suspension device as defined in claim 1, wherein the harness support portion includes a back portion and a pair of shoulder portions extending each from the back portion, the back and shoulder portions being configured and sized for extending respectively substantially parallel to a back and over the shoulders of the intended user when the harness is operatively worn by the intended user.

11. The suspension device as defined in claim 10, wherein the harness attachment is secured to the back portion.

12. The suspension device as defined in claim 1, wherein the support is mountable to a ceiling.

13. The suspension device as defined in claim 12, wherein the support includes a base mountable to the ceiling and an arm mounted to the base, the elongated flexible element being mounted to the arm.

14. The suspension device as defined in claim 13, wherein the arm is pivotable relative to the base about a substantially vertical axis when the support is operatively mounted to the ceiling.

15. The suspension device as defined in claim 13, wherein the arm is telescopic so that a distance between the elongated flexible element and the base is varied as the arm is extended and retracted.

16. The suspension device as defined in claim 1, further comprising a balancer between the elongated flexible element and the support.

17. The suspension device as defined in claim 1, wherein the elongated flexible element is a cable.

18. A suspended radioprotection garment, comprising:
the suspension device as defined in claim 1; and
a radioprotection garment at least partially supported by the suspension device.

19. The suspended radioprotection garment as defined in claim 18, wherein the radioprotection garment is worn over the harness.

20. A suspension device for at least partially supporting a radioprotection garment while the radioprotection garment is worn by an intended user, the suspension device comprising:
a harness wearable by the intended user under the radioprotection garment, the harness including a harness attachment;
a support positionable above the intended user;
an elongated flexible element operatively coupled to the support to be supported thereby;
a flexible element attachment secured to the elongated flexible element opposed to the support;
the harness and flexible element attachment being reversibly attachable to each other;
wherein, when the harness and flexible element attachments are attached to each other and a tension is applied to the elongated flexible element, at least part of a weight of the radioprotection garment is supported by the support through the elongated flexible element;
further wherein
the harness includes a substantially rigid harness support portion, the harness attachment being secured to the harness support portion;
the flexible element attachment includes an attachment portion attachable to the harness attachment and a linking portion extending from the attachment portion, the linking portion defining a flexible element receiving portion, the elongated flexible element being secured to the flexible element receiving portion;
the harness attachment includes an anterior abutment portion and a posterior abutment portion defining a gap therebetween, the anterior abutment portion being closer to the harness support portion than the posterior abutment portion, the posterior abutment portion being higher than the anterior abutment portion when the suspension device is operatively used to support the radioprotection garment;

the attachment portion defines an anterior abutment surface and a posterior abutment surface;

the attachment portion is insertable in the gap between the anterior and posterior abutment portions and movable relative thereto between an engaged position and a disengaged position, wherein, in the engaged position, the anterior and posterior abutment surfaces abut respectively against the anterior and posterior abutment portions, and in the disengaged position, at least one of the anterior and posterior abutment surfaces is spaced apart from respectively the anterior and posterior abutment portions to allow removal of the attachment portion;

the harness attachment includes a frame, an anterior abutment member mounted to the frame and a posterior abutment member mounted to the frame, the anterior and posterior abutment members defining respectively the anterior and posterior abutment portions;

the anterior and posterior abutment members are substantially elongated and substantially parallel to each other; and the attachment portion is substantially plate-shaped and defines a concave groove defining the anterior abutment surface and receiving the anterior abutment member thereinto in the engaged position.

\* \* \* \* \*